US012156907B2

(12) United States Patent
Sohn et al.

(10) Patent No.: US 12,156,907 B2
(45) Date of Patent: Dec. 3, 2024

(54) RECOMBINANT VECTOR FOR EXPRESSING VIRUS-LIKE PARTICLES IN PLANT AND METHOD FOR PREPARATION OF VACCINE COMPOSITION CONTAINING CIRCOVIRUS-LIKE PARTICLES BY USING SAME

(71) Applicant: BIOAPPLICATIONS INC., Gyeongsangbuk-do (KR)

(72) Inventors: Eun-Ju Sohn, Gyeongsangbuk-do (KR); Yongjik Lee, Gyeongsangbuk-do (KR); Sangmin Lee, Gyeongsangbuk-do (KR)

(73) Assignee: BIOAPPLICATIONS INC., Gyeongsangbuk-do (KR)

( * ) Notice: Subject to any disclaimer, the term of this patent is extended or adjusted under 35 U.S.C. 154(b) by 651 days.

(21) Appl. No.: 17/320,369

(22) Filed: May 14, 2021

(65) Prior Publication Data

US 2021/0330780 A1  Oct. 28, 2021

Related U.S. Application Data

(63) Continuation-in-part of application No. PCT/KR2019/013581, filed on Oct. 16, 2019.

(30) Foreign Application Priority Data

Nov. 15, 2018 (KR) .......................... 10-2018-0141184
Oct. 15, 2019 (KR) .......................... 10-2019-0127987

(51) Int. Cl.
| | |
|---|---|
| *A61K 39/12* | (2006.01) |
| *A61K 39/00* | (2006.01) |
| *C12N 15/82* | (2006.01) |

(52) U.S. Cl.
CPC .......... *A61K 39/12* (2013.01); *C12N 15/8205* (2013.01); *A61K 2039/55505* (2013.01); *C12N 2750/10023* (2013.01); *C12N 2750/10034* (2013.01); *C12N 2750/10051* (2013.01)

(58) Field of Classification Search
CPC .......... A61K 39/12; A61K 2039/55505; A61K 2039/5258; C12N 15/8205; C12N 2750/10023; C12N 2750/10034; C12N 2750/10051; C12N 2750/10022; C12N 15/8221; C12N 15/8257; C12N 15/8258; C07K 2319/02; C07K 14/005; C07K 14/415; A61P 31/12

See application file for complete search history.

(56) References Cited

U.S. PATENT DOCUMENTS

| | | | |
|---|---|---|---|
| 2009/0017064 A1 | 1/2009 | Wu | |
| 2014/0322267 A1 | 10/2014 | Haiwick | |
| 2017/0335361 A1 * | 11/2017 | Hwang | ............... C07K 14/5759 |

FOREIGN PATENT DOCUMENTS

| | | | | |
|---|---|---|---|---|
| CN | 102146139 A | 8/2011 | | |
| CN | 106478783 A | 3/2017 | | |
| CN | 107384948 A | 11/2017 | | |
| CN | 108135142 A | 6/2018 | | |
| KR | 10-0233191 B1 | 12/1999 | | |
| KR | 20030007221 A | 1/2003 | | |
| KR | 10-2006-0011675 A | 2/2006 | | |
| KR | 20060011675 A | 2/2006 | | |
| KR | 10-1449155 B1 | 10/2014 | | |
| KR | 10-2015-0113934 A | 10/2015 | | |
| KR | 10-2017-0131207 A | 11/2017 | | |
| KR | 20170131207 A | 11/2017 | | |
| KR | 10-1848082 B1 | 4/2018 | | |
| KR | 10-2018-0084680 B1 | 9/2019 | | |
| WO | WO-0206497 A2 * | 1/2002 | ............. | C07K 14/57 |
| WO | 2008151215 A1 | 12/2008 | | |
| WO | 2014201321 A1 | 12/2014 | | |
| WO | WO-2017106736 A1 * | 6/2017 | | |
| WO | 2018050872 A1 | 3/2018 | | |
| WO | 2018180568 A1 | 10/2018 | | |

OTHER PUBLICATIONS

Rashid, A., K. Rasheed, and M. Akhtar. "Factors Influencing Vaccine Efficacy—A General Review." J. Anim. Plant Sci 19 (2009): 22-25. (Year: 2009).*

Kim, S., Lee, DS., Choi, I.S et al. *Arabidopsis thaliana* Rubisco small subunit transit peptide increases the accumulation of Thermotoga maritima endoglucanase Cel5A in chloroplasts of transgenic tobacco plants. Transgenic Res 19, 489-497 (2010). https://doi.org/10.1007/s11248-009-9330-8 (Year: 2010).*

(Continued)

*Primary Examiner* — Charles Logsdon
*Assistant Examiner* — Kelsey L McWilliams
(74) *Attorney, Agent, or Firm* — Riverside Law LLP

(57) ABSTRACT

The present invention relates to a technique of preparing a vaccine composition from PCV2 isolated from a plant transformed with a chlorophyll-targeting recombinant vector for expression in plants and provides a recombinant vector carrying a polynucleotide coding for a recombinant protein in which a chlorophyll-targeting protein and a PCV2 capsid protein are fused to each other. In addition, provided are a transgenic plant transformed with the recombinant vector, a method for isolating and purifying a target protein from the transgenic plant, a method for preparing a vaccine composition containing virus-like particles by using same, and a vaccine composition prepared by the preparation method.

19 Claims, 6 Drawing Sheets

Specification includes a Sequence Listing.

(56) References Cited

OTHER PUBLICATIONS

Santi, Luca, et al. "An efficient plant viral expression system generating orally immunogenic Norwalk virus-like particles." Vaccine 26.15 (2008): 1846-1854. (Year: 2008).*
Peyret, Hadrien. "A protocol for the gentle purification of virus-like particles produced in plants." Journal of virological methods 225 (2015): 59-63. (Year: 2015).*
Quan, Fu-Shi, et al. "Mucosal adjuvants for influenza virus-like particle vaccine." Viral immunology 26.6 (2013): 385-395. (Year: 2013).*
Chinese Office Action Issued in App. No. CN201980075026.3, dated May 5, 2023, 8 Pages.
Xiao C.T , "capsid protein [Porcine circovirus 2]", GenBank DataBase, p. 41437.
Suyeon Kim , "*Arabidopsis thaliana* Rubisaco smalltransit peptide increases the accumulation of Thermptoga maritima endoglucanase Cel5A in choloroplasts of transgenic tobacco plants", Transgenic Research, vol. 19, No. 3, p. 490.
Kim, S., et al., "*Arabidopsis thaliana* Rubisco small subunit transit peptide increases the accumulation of Thermotoga maritima endoglucanase Cel5A in chloroplasts of transgenic tobacco plants", Transgenic Research, 2010, 19: 489-497.
GenBank Accession No. A0D41437.1, dated Jun. 13, 2017; https://www.ncbi.nlm.nih.gov/protein/AOD41437.1.
GenBank Accession No. AEP19975.1, dated Jul. 25, 2016; https://www.ncbi.nlm.nih.gov/protein/AEP19975.1.
Databse Uniprot (Online), Accession No. Q8JMU0, <https://www.uniprot.org/uniprot/Q8JMU0.txt?version=22>, Uploaded Apr. 25, 2018, Choi, J. et al., Definition: Capsid protein.
Japanese Office ACtion issued in App. No. JP2021-526675, May 26, 2022, 6 pages.
Kim, S., et al., "*Arabidopsis thaliana* Rubisco small subunit transit peptide increases the accumulation of Thermotoga maritima endoclucanase Cel5A in chloroplasts of transgenic tobacco plants", Transgenic Research, vol. 19 (2010), pp. 489-497.
Extended European Search Report issued in App. No. EP19884354.2, dated Jul. 5, 2022, 7 pages.

\* cited by examiner

```
                         SEQUENCE LISTING

<160> NUMBER OF SEQ ID NOS: 12

<210> SEQ ID NO 1
<211> LENGTH: 25
<212> TYPE: PRT
<213> ORGANISM: Artificial Sequence
<220> FEATURE:
<223> OTHER INFORMATION: Amino acid sequence of RuBisCO transit peptide

<400> SEQUENCE: 1

Cys Met Gln Val Trp Pro Pro Ile Gly Lys Lys Lys Phe Glu Thr Leu
1               5                   10                  15

Ser Tyr Leu Pro Asp Leu Thr Asp Ser
            20                  25

<210> SEQ ID NO 2
<211> LENGTH: 237
<212> TYPE: DNA
<213> ORGANISM: Artificial Sequence
<220> FEATURE:
<223> OTHER INFORMATION: DNA sequence of RuBisCO transit peptide

<400> SEQUENCE: 2
atggcttcct ctatgctctc ttccgctact atggttgcct ctccggctca ggccactatg      60
gtcgctcctt tcaacggact taagtcctcc gctgccttcc cagccacccg caaggctaac     120
aacgacacta cttccatcac aagcaacggc ggaagagtta actgcatgca ggtgtggcct     180
ccgattggaa agaagaagtt tgagactctc tcttaccttc ctgaccttac cgattcc        237

<210> SEQ ID NO 3
<211> LENGTH: 192
<212> TYPE: PRT
<213> ORGANISM: Artificial Sequence
<220> FEATURE:
<223> OTHER INFORMATION: Amino acid sequence of PCV2

<400> SEQUENCE: 3
```

```
Asn Gly Ile Phe Asn Thr Arg Leu Ser Arg Thr Phe Gly Tyr Thr Val
1               5                   10                  15

Lys Arg Thr Thr Val Thr Thr Pro Ser Trp Ala Val Asp Met Met Arg
            20                  25                  30

Phe Lys Leu Asp Asp Phe Val Pro Pro Gly Gly Gly Thr Asn Lys Ile
        35                  40                  45

Ser Ile Pro Phe Glu Tyr Tyr Arg Ile Arg Lys Val Lys Val Glu Phe
    50                  55                  60

Trp Pro Cys Ser Pro Ile Thr Gln Gly Asp Arg Gly Val Gly Ser Thr
65                  70                  75                  80

Ala Val Ile Leu Asp Asp Asn Phe Val Pro Lys Ala Asn Ala Leu Thr
                85                  90                  95

Tyr Asp Pro Tyr Val Asn Tyr Ser Ser Arg His Thr Ile Pro Gln Pro
            100                 105                 110

Phe Ser Tyr His Ser Arg Tyr Phe Thr Pro Lys Pro Val Leu Asp Ser
        115                 120                 125

Thr Ile Asp Tyr Phe Gln Pro Asn Asn Lys Arg Asn Gln Leu Trp Leu
    130                 135                 140

Arg Leu Gln Thr Ser Arg Asn Val Asp His Val Gly Leu Gly Thr Ala
145                 150                 155                 160

Phe Glu Asn Ser Lys Tyr Asp Gln Asp Tyr Asn Ile Arg Val Thr Met
                165                 170                 175

Tyr Val Gln Phe Arg Glu Phe Asn Leu Lys Asp Pro Pro Leu Asn Pro
            180                 185                 190

<210> SEQ ID NO 4
<211> LENGTH: 579
<212> TYPE: DNA
<213> ORGANISM: Artificial Sequence
<220> FEATURE:
<223> OTHER INFORMATION: DNA sequence of PCV2

<400> SEQUENCE: 4
aatggcattt tcaatacacg cctcagtcga acttttggat atactgtcaa gcgtactaca      60
gtcaccacgc catcttgggc tgtggatatg atgagattta agttggatga ctttgttcct     120
cctggagggg gaaccaacaa aatttctata ccgtttgagt actatagaat cagaaaagtt     180
aaggttgagt ctggccgtgt tccccccata actcagggtg ataggggtgt gggttcaact     240
gctgttattc tagatgataa cttcgtacct aaggccaacg cattgactta tgaccctat      300 gtaaactact catctagaca tacaatccca caacctttct cctaccactc gcgttatttt     360
acaccaaagc ctgtttttaga ttctaccatt gattatttcc aaccaaataa caagaggaat     420
cagctttggt tgagattaca aacctcacgg aacgtggatc atgtcggatt gggtactgca     480
tttgaaaata gtaagtatga tcaggactac aatatccgtg tgacaatgta cgttcaattt     540
agggaattta atcttaaaga cccaccactt aatccatag                            579

<210> SEQ ID NO 5
<211> LENGTH: 233
<212> TYPE: PRT
<213> ORGANISM: Artificial Sequence
<220> FEATURE:
<223> OTHER INFORMATION: Amino acid sequence of PCV2b

<400> SEQUENCE: 5

Met Thr Tyr Pro Arg Arg Arg Tyr Arg Arg Arg His Arg Pro Arg
1               5                   10                  15
```

-continued

Ser His Leu Gly Gln Ile Leu Arg Arg Arg Pro Trp Leu Val His Pro
            20                  25                  30

Arg His Arg Tyr Arg Trp Arg Lys Asn Gly Ile Phe Asn Thr Arg
        35                  40                  45

Leu Ser Arg Thr Phe Gly Tyr Thr Ile Lys Arg Thr Thr Val Arg Thr
    50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Arg Ser Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Ser Ala Val Ile Leu Asp Asp Asn
            115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
    195                 200                 205

Gln Glu Tyr Asn Ile Arg Val Thr Met Tyr Val Gln Phe Arg Glu Phe
    210                 215                 220

Asn Leu Lys Asp Pro Pro Leu Asn Pro
225                 230

<210> SEQ ID NO 6
<211> LENGTH: 702
<212> TYPE: DNA
<213> ORGANISM: Artificial Sequence
<220> FEATURE:
<223> OTHER INFORMATION: DNA sequence of PCV2b

<400> SEQUENCE: 6

```
atgacgtatc caaggaggcg ttaccggaga agaagacacc gcccccgcag ccatcttggc    60
cagatcctcc gccgccgccc ctggctcgtc caccccgcc accgttaccg ctggagaagg    120
aaaaatggca tcttcaacac ccgcctatcc cgcaccttcg gatatactat caagcgaacc    180
acagtcaaaa cgccctcctg gcggtggac atgatgagat tcaatattaa tgactttctt    240
cccccaggag ggggctcaaa ccccgctct gtgccctttg aatactacag aataagaaag    300
gttaaggtcg aattctggcc ctgctccccg atcacccagg gtgacagggg agtgggctcc    360
agtgctgtta ttctagatga taactttgta acaaaggcca cagccctcac ctatgacccc    420
tacgtaaact actcctcccg ccataccata acccagccct ctcctacca ctcccgctac    480
tttaccccca aacctgtcct agattccact attgattact ccaaccaaa caacaaaga    540
aaccagctgt ggctgagact acaaactgct ggaaatgtag accacgtagg cctcggcact    600
gcgttcgaaa acagtatata cgaccaagaa tacaatatcc gtgtaaccat gtatgtacaa    660
ttcagagaat ttaatcttaa agacccccca cttaaccctt aa                      702
```

<210> SEQ ID NO 7
<211> LENGTH: 6

-continued

```
<212> TYPE: PRT
<213> ORGANISM: Artificial Sequence
<220> FEATURE:
<223> OTHER INFORMATION: Amino acid sequence of polyhistidine-tag

<400> SEQUENCE: 7

His His His His His His
1               5

<210> SEQ ID NO 8
<211> LENGTH: 18
<212> TYPE: DNA
<213> ORGANISM: Artificial Sequence
<220> FEATURE:
<223> OTHER INFORMATION: DNA sequence of polyhistidine-tag

<400> SEQUENCE: 8
caccaccatc accaccat                                                    18

<210> SEQ ID NO 9
<211> LENGTH: 41
<212> TYPE: PRT
<213> ORGANISM: Artificial Sequence
<220> FEATURE:
<223> OTHER INFORMATION: Amino acid sequence of BiP signal peptide

<400> SEQUENCE: 9

Met Ala Arg Ser Phe Gly Ala Asn Ser Thr Val Val Leu Ala Ile Ile
1               5                   10                  15

Phe Phe Gly Cys Leu Phe Ala Leu Ser Ser Ala Ile Glu Glu Ala Thr
            20                  25                  30

Lys Leu Gly Ser Val Ile Gly Ile Asp
        35                  40

<210> SEQ ID NO 10
<211> LENGTH: 123
<212> TYPE: DNA
<213> ORGANISM: Artificial Sequence
<220> FEATURE:
<223> OTHER INFORMATION: DNA sequence of BiP signal peptide

<400> SEQUENCE: 10
atggctcgct cgtttggagc taacagtacc gttgtgttgg cgatcatctt cttcggatgt      60
ttatttgcgt tgtcctctgc aatagaagag gctacgaagt taggatcagt gatagggata     120
gat                                                                   123

<210> SEQ ID NO 11
<211> LENGTH: 4
<212> TYPE: PRT
<213> ORGANISM: Artificial Sequence
<220> FEATURE:
<223> OTHER INFORMATION: Amino acid sequence of HDEL

<400> SEQUENCE: 11

His Asp Glu Leu
1

<210> SEQ ID NO 12
<211> LENGTH: 12
<212> TYPE: DNA
<213> ORGANISM: Artificial Sequence
```

-continued

```
<220> FEATURE:
<223> OTHER INFORMATION: DNA sequence of HDEL

<400> SEQUENCE: 12
catgatgagc tc                                                    12
```

RECOMBINANT VECTOR FOR EXPRESSING VIRUS-LIKE PARTICLES IN PLANT AND METHOD FOR PREPARATION OF VACCINE COMPOSITION CONTAINING CIRCOVIRUS-LIKE PARTICLES BY USING SAME

CROSS-REFERENCE TO RELATED APPLICATIONS

This application is a continuation-in-part of International Patent Application No. PCT/KR2019/013581, filed Oct. 16, 2019, which claims the benefit of priority from Korean Patent Application No. 10-2018-0141184, filed on Nov. 15, 2018 and Korean Patent Application No. 10-2019-0127987 filed on Oct. 15, 2019, the contents of each of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0115-00US Sequence Listing.txt" in ASCII format. The text file containing the Sequence Listing of the present application was created on May 4, 2021 and is 8,751 bytes in size.

TECHNICAL FIELD

The present invention relates to a vaccine composition containing virus-like particles (VLPs) produced using a plant, and more specifically, to a method for preparing virus-like particles as a vaccine composition by enhancing the productivity of a porcine circovirus type 2 (PCV2) capsid protein that can be used as a vaccine composition using a highly efficient expression vector in plants, and simultaneously making the produced PCV2 capsid protein into the virus-like particles.

This application claims priority to and the benefit of Korean Patent Application Nos. 10-2018-0141184 and 10-2019-0127987 filed in the Korean Intellectual Property Office on Nov. 15, 2018 and Oct. 15, 2019, respectively, and all the contents disclosed in the specifications and drawings of those applications are incorporated in this application.

BACKGROUND ART

In general, the production of a useful bioactive material using a transgenic plant can fundamentally eliminate various contaminants such as viruses, oncogenes, and enterotoxins, which may be generated by a method of synthesizing and producing proteins from animal cells and microorganisms, and when the demand for the corresponding useful material increases rapidly, a system of producing a useful bioactive material using a transformed plant is absolutely advantageous compared to existing animal cell systems in terms of equipment technology or costs required for mass production, so that recently, the system has been widely used in various research fields such as basic science research, vaccine development, and therapeutic agent development due to an advantage where it is possible to achieve mass production in the shortest time at low cost.

However, despite the advantage presented above, relatively low protein expression levels and non-optimized isolation and purification methods are the major obstacles to the production of proteins from plant cells, compared to other hosts including animal cells and microorganisms. Thus, many studies have been conducted, and attempts are being made to increase the relatively low expression and productivity of proteins from plant cells by various methods. Examples thereof include a vector construction technique for efficiently transferring foreign genes into plants or increasing the expression level of a target protein, a transformation technique for allowing plants to synthesize a target protein, a protein isolation and purification technique that enables a target protein to be produced from transformants, and the like.

Here, as an example of the vector production technique for efficiently transferring a foreign gene into a plant or enhancing the expression of a target protein as described above, Korean Registered Patent No. 10-1449155 suggested that by adding a DNA fragment upstream of a target protein to be produced as a recombinant vector, a plant transformed with the recombinant vector can improve the translation of the target protein, allows the target protein to be stably accumulated by inducing migration to a specific location in the plant, and there is an effect of being able to produce the target protein in a large amount from the plant for these reasons.

Further, as another example of the related art for the vector production technique for increasing the expression level of a protein, Korean Published Patent No. 10-2018-0084680 suggested a method of allowing the expression level of a protein to be increased when a small domain that causes N-glycosylation is fused with a target protein, thereby dramatically increasing the target protein production efficiency in a transgenic plant, as a method of increasing the expression level of the target protein in the translation stage when the target protein is produced from plant cells.

Furthermore, as an example of a protein isolation and purification technique that enables a target protein to be produced from transformants, Korean Registered Patent No. 10-1848082 suggested that a fusion protein including a target protein can be isolated by binding proteins synthesized from transgenic plants to cellulose using a recombinant vector including cellulose-binding domain 3 and the recombinant vector, and the target protein and the cellulose-binding domain can be efficiently separated by treating the fusion protein with an enterokinase.

Further, as another example of a protein isolation and purification technique that enables a target protein to be produced, Korean Published Patent No. 10-2015-0113934 suggested that when a bioactive protein or peptide is bound to an immunoglobulin Fc fragment, there is an effect of improving the solubility of the bioactive protein or peptide compared to a bioactive protein or peptide to which the immunoglobulin Fc fragment is not bound.

Therefore, when a useful bioactive material is produced from a plant based on the above-described conventional techniques, there is an effect that a production method using animal cells and microorganisms, which is an existing method, can be replaced. First, the period required for the production of a useful bioactive material can be shortened, and the production costs can be dramatically reduced. Second, it is possible to fundamentally eliminate a contaminant causing cytotoxicity which may occur in the process of isolating and purifying a protein synthesized from animal cells and microorganisms, and third, when commercialized, the useful bioactive material produced from a plant can be stored in the form of seeds for a long period of time, and storage and preservation costs can be reduced. Fourth, the useful bioactive material can be transported in the form of safe seeds and can be quickly supplied to a region or country where it is needed in the event of an urgent problem. Fifth, when the demand for the bioactive material increases rapidly, the material can be easily mass-produced because many technologies are not required for the production equipment and system construction required for mass production, and there is an advantage where it is possible to dramatically lower installation costs and product production costs, enable mass production in the shortest time to enable sufficient supply according to demand.

In addition, the plant system has a synthetic route that causes a post-translational modification process, which is essential in mammals, so that there is an advantage in that it is possible to produce a form similar to that of a protein produced using animal cells. Therefore, a method of producing a protein, which is a useful bioactive material, using such a transgenic plant as described above has the potential to replace a method of producing the protein using animal cells or microorganisms, thus attracting great attention recently.

As described above, although various techniques for effectively synthesizing, isolating and purifying useful bioactive materials including medically applicable proteins and vaccines, and industrially useful enzymes from plants are provided, each protein has different inherent characteristics, so that there is a need for individual studies because it is not preferable to collectively apply a specific method.

DISCLOSURE

Technical Problem

The present invention has been made to solve the problems in the related art as described above, and confirmed that in producing porcine circovirus type 2 (PCV2) that forms virus-like particles as a target protein in a transformed plant, when a RuBisCO transit peptide is fused to the target protein and polyhistidine was attached for isolation and purification so as to be targeted to chloroplasts in order to increase the expression level of the protein in the translation stage, the expression level and isolation and purification efficiency of the protein were increased, and confirmed that target protein production efficiency could be dramatically increased in the transgenic plant using the same.

Furthermore, it was confirmed by various experimental methods that virus-like particles were formed when the pH of a solution including PCV2 isolated and purified as described above was appropriately adjusted, and the present invention was completed by demonstrating that such virus-like particles could enhance the formation of neutralizing antibodies which neutralize viruses.

Thus, an object of the present invention is to provide a recombinant vector for plant expression, including a polynucleotide encoding a RuBisCO transit peptide including an amino acid sequence represented by SEQ ID NO: 1 and a polynucleotide encoding a porcine circovirus type 2 (PCV2) capsid protein including an amino acid sequence represented by SEQ ID NO: 3 or 5.

Another object of the present invention is to provide a transgenic plant transformed with the recombinant vector of the present invention.

Further, still another object of the present invention is to provide a method for isolating and purifying a recombinant PCV2 capsid protein, the method including the following steps:

(S1) transforming a plant using the recombinant vector of the present invention;
(S2) preparing a plant mixture solution by mixing the transgenic plant obtained in Step (S1) with a protein extraction buffer solution:
(S3) adsorbing a recombinant protein in which a polyhistidine-tag is linked to the PCV2 capsid protein by injecting the mixture solution obtained in Step (S2) into a column packed with agarose;
(S4) washing the column by injecting a washing solution into the column; and
(S5) eluting the recombinant protein adsorbed onto agarose by injecting an elution solution into the column.

In addition, yet another object of the present invention is to provide a method for preparing a vaccine composition containing virus-like particles, the method including the following steps:

(S1) transforming a plant using the recombinant vector of the present invention;
(S2) isolating and purifying a PCV2 capsid protein from the transgenic plant obtained in Step (S1);
(S3) making the PCV2 capsid protein obtained in Step (S2) into virus-like particles; and
(S4) preparing a vaccine composition containing the virus-like particles obtained in Step (S3).

Furthermore, yet another object of the present invention is to provide a vaccine composition prepared by the preparation method according to the present invention.

Further, yet another object of the present invention is to provide PCV2 virus-like particles contained in a vaccine composition prepared by the preparation method of the present invention.

In addition, yet another object of the present invention is to provide a method for preventing porcine circovirus infection by administering a vaccine composition prepared by the preparation method according to the present invention to an individual.

Yet another object of the present invention is to provide a use of a vaccine composition prepared by the preparation method according to the present invention for preventing porcine circovirus infection.

Yet another object of the present invention is to provide a use of a composition prepared by the preparation method according to the present invention for producing a vaccine used for preventing porcine circovirus infection.

However, the technical problems which the present invention intends to solve are not limited to the technical problems which have been mentioned above, and other technical problems which have not been mentioned will be clearly understood by a person with ordinary skill in the art to which the present invention pertains from the following description.

Technical Solution

To achieve the objects of the present invention as described above, the present invention provides a recombinant vector for plant expression, including a polynucleotide encoding a RuBisCO transit peptide including an amino acid sequence represented by SEQ ID NO: 1 and a polynucleotide encoding a porcine circovirus type 2 (PCV2) capsid protein including an amino acid sequence represented by SEQ ID NO: 3 or 5.

As an exemplary embodiment of the present invention, the polynucleotide encoding the RuBisCO transit peptide may include a base sequence represented by SEQ ID NO: 2. Furthermore, the polynucleotide encoding the PCV2 capsid protein may include a base sequence represented by SEQ ID NO: 4 or SEQ ID NO: 6.

As another exemplary embodiment of the present invention, the recombinant vector may further include a polynucleotide encoding a polyhistidine-tag including an amino acid sequence represented by SEQ ID NO: 7.

As still another exemplary embodiment of the present invention, in the recombinant vector, a polynucleotide encoding a RuBisCO transit peptide, a polynucleotide encoding a polyhistidine-tag, and a polynucleotide encoding a PCV2 capsid protein are sequentially connected between a promoter and a terminator, but the order of connection is not limited thereto.

The present invention also provides a transgenic plant transformed with the recombinant vector of the present invention.

Further, the present invention provides a method for isolating and purifying a recombinant PCV2 capsid protein, the method including the following steps:

(S1) transforming a plant using the recombinant vector of the present invention:

(S2) preparing a plant mixture solution by mixing the transgenic plant obtained in Step (S1) with a protein extraction buffer solution;

(S3) adsorbing a recombinant protein in which a polyhistidine-tag is linked to the PCV2 capsid protein by injecting the mixture solution obtained in Step (S2) into a column packed with agarose;

(S4) washing the column by injecting a washing solution into the column; and (S5) eluting the recombinant protein adsorbed onto agarose by injecting an elution solution into the column.

As an exemplary embodiment of the present invention, the protein extraction buffer solution may include 10 to 100 mM Tris, 100 to 300 mM sodium chloride (NaCl), 0.01 to 0.5% Triton X-100(polyethylene glycol p-(1,1,3,3-tetramethylbutyl)-phenylether, and 5 to 300 mM imidazole.

As another exemplary embodiment of the present invention, the agarose may be nickel-nitrilotriacetic acid (Ni-NTA) agarose.

Still another exemplary embodiment of the present invention, Step (S1) may transform a plant using a bacterium into which a recombinant vector is introduced, and the bacterium may be preferably *Agrobacterium tumefaciens*.

In addition, the present invention provides a method for preparing a vaccine composition containing virus-like particles, the method including the following steps:

(S1) transforming a plant using the recombinant vector of the present invention;

(S2) isolating and purifying a PCV2 capsid protein from the transgenic plant obtained in Step (S1);

(S3) making the PCV2 capsid protein obtained in Step (S2) into virus-like particles; and (S4) preparing a vaccine composition containing the virus-like particles obtained in Step (S3).

As an exemplary embodiment of the present invention, the method for preparing a vaccine composition may further include adding an adjuvant. Alum may be used as the adjuvant, but the adjuvant is not limited thereto.

As another exemplary embodiment of the present invention, the plant may be a dicotyledonous plant selected from the group consisting of *Arabidopsis thaliana*, soybean, tobacco, eggplant, capsicum, potato, tomato, Chinese cabbage, cabbage, and lettuce; or a monocotyledonous plant selected from the group consisting of rice, barley, wheat, rye, corn, sugar cane, oats, and onion.

As still another exemplary embodiment of the present invention, Step (S1) may transform a plant using a bacterium into which a recombinant vector is introduced, and the bacterium may be preferably *Agrobacterium tumefaciens*, but is not limited thereto.

As yet another exemplary embodiment of the present invention, Step (S3) may make virus-like particles by changing a pH of a buffer solution including a PCV2 capsid protein.

As yet another exemplary embodiment of the present invention, the buffer solution may include 50 to 100 mM Tris, 300 to 1000 mM sodium chloride (NaCl), and 10 to 100 mM arginine, and may have a pH of 6.9 to 7.5.

As yet another exemplary embodiment of the present invention, the pH of the buffer solution may be preferably 7.2.

Furthermore, the present invention provides a vaccine composition prepared by the preparation method according to the present invention.

As an exemplary embodiment of the present invention, the vaccine composition may further an adjuvant. The adjuvant may be alum, but is not limited thereto.

Further, the present invention provides PCV2 virus-like particles contained in a vaccine composition prepared by the preparation method of the present invention.

As an exemplary embodiment of the present invention, the PCV2 virus-like particles are shown to have a molecular weight of about 2,000 kDa by size-exclusion chromatography and 669 kDa or more by polyacrylamide gel electrophoresis (Native-PAGE), and may be a spherical or ring form having a diameter of 10 nm or more and 40 nm or less, preferably 20 nm or more and 30 nm or less when stained by a negative staining method, and then observed by a transmission electron microscope.

In addition, the present invention provides a method for preventing porcine circovirus infection by administering a vaccine composition prepared by the preparation method according to the present invention to an individual.

Furthermore, the present invention provides a use of a vaccine composition prepared by the preparation method according to the present invention for preventing porcine circovirus infection.

Further, the present invention provides a use of a composition prepared by the preparation method according to the present invention for producing a vaccine used for preventing porcine circovirus infection.

Advantageous Effects

The present invention relates to a PCV2 vaccine composition containing virus-like particles prepared using a plant expression vector targeted to chloroplasts, and can remarkably reduce production costs and can fundamentally block various contaminants (viruses, oncogenes, enterotoxins, and the like) which may be generated by a method widely known in the related art (a method of producing a protein from animal cells or microorganisms, and then isolating and purifying the protein). In addition, since the present invention includes a synthetic route for an eukaryotic protein in which a post-translational transformation process, which animal cells essentially include, occurs, the present invention is advantageous in that it is possible to produce a protein that maintains physiological activity, and even in the commercialization stage, the product can be managed as a seed stock unlike animal cells or bacteria. Furthermore, when the demand for the corresponding material increases rapidly, the present invention is more efficient and economical than an existing production system using animal cells or bacteria in terms of equipment technology and costs required for mass production, so that there is also an advantage in that the corresponding material can be mass-produced and supplied in a short period of time as demand arises.

MODES OF THE INVENTION

Figure 1:
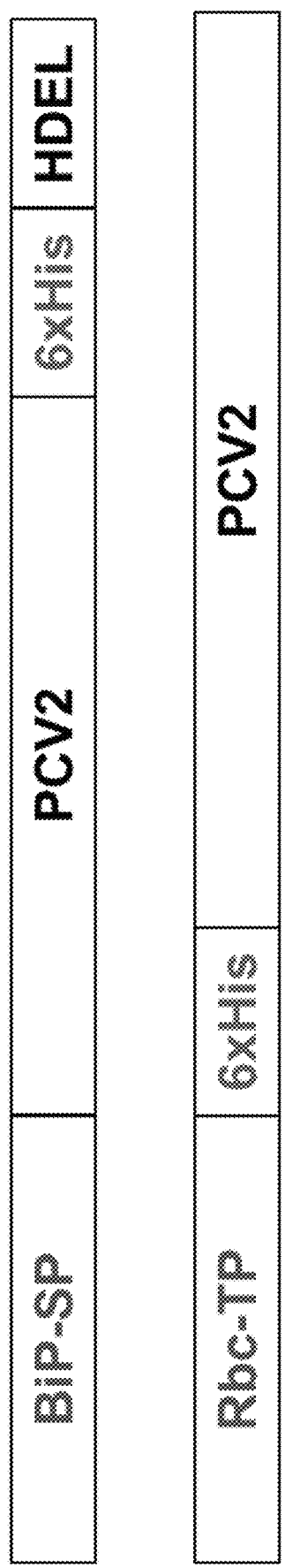
FIG. 1 is a view illustrating expression cassettes of two recombinant PCV2 capsid proteins for expression of the recombinant PCV2 capsid protein in a plant according to an exemplary embodiment of the present invention. (Rbc-TP, RuBisCO transit peptide; 6×His, polyhistidine-tag; BiP—SP, chaperone binding protein signal peptide).

The present inventors confirmed that in producing porcine circovirus type 2 (PCV2) that forms virus-like particles as a target protein in a transformed plant, when a RuBisCO transit peptide is fused to the target protein and polyhistidine was attached for isolation and purification so as to be targeted to chloroplasts in order to increase the expression level of the protein in the translation stage, the expression level and isolation and purification efficiency of the protein were increased, and confirmed that target protein production efficiency could be dramatically increased in the transgenic plant using the same, thereby completing the present invention.

Thus, in an exemplary embodiment of the present invention, a plant expression vector expressing a recombinant protein in which a polyhistidine-tag and a chloroplast-targeted RuBisCO transit peptide were fused to a PCV2 capsid protein and a plant expression vector expressing a recombinant protein in which a polyhistidine-tag and an endoplasmic reticulum-targeted chaperone binding protein (BiP) signal peptide were fused to a PCV2 capsid protein were constructed (see Example 1).

In another exemplary embodiment of the present invention, after *Agrobacterium* was transformed with the plant expression vector, the recombinant PCV2 capsid protein was expressed in a plant by injecting the transformed *Agrobacterium* into the backside of leaves of *Nicotiana benthamiana* (see Example 2).

In still another exemplary embodiment of the present invention, a recombinant protein was isolated and purified from *Nicotiana benthamiana* leaves expressing the recombinant PCV2 capsid protein using a column packed with an Ni-NTA agarose resin, and the self-assembly of the PCV2 capsid protein was induced from the recombinant protein using a buffer solution for making virus-like particles (see Examples 3 to 5).

In yet another exemplary embodiment of the present invention, it was confirmed that an antibody against PCV2 was formed by injecting a composition containing the PCV2 virus-like particles obtained above into guinea pigs (see Example 6).

In yet another exemplary embodiment of the present invention, it was confirmed that both PCV2a and PCV2b genotypes had an ability to form virus neutralizing antibodies by administering a composition containing PCV2 virus-like particles of the two genotypes to guinea pigs (see Example 7).

Thus, the present invention may provide a recombinant vector for plant expression, including a polynucleotide encoding a RuBisCO transit peptide including an amino acid sequence represented by SEQ ID NO: 1 and a polynucleotide encoding a porcine circovirus type 2 (PCV2) capsid protein including an amino acid sequence represented by SEQ ID NO: 3 or 5.

As used herein, the term "RuBisCo transit peptide" refers to an N-terminal transit peptide of the small subunit of Ribulose-1,5-Bisphosphate Carboxylase/Oxygenase, and is preferably encoded by a polynucleotide including a base sequence of SEQ ID NO: 2, most preferably encoded by a polynucleotide represented by SEQ ID NO: 2, but may be encoded by a base sequence having a sequence homology of 80% or more, more preferably 90% or more, and even more preferably 95% or more to the base sequence of SEQ ID NO: 2. For example, the RuBisCo transit peptide includes a polypeptide having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. The % sequence homology to a polynucleotide is confirmed by comparing a comparison region with an optimally aligned sequence, and a portion of the polynucleotide sequence in the comparison region may include an addition or deletion (that is, a gap) compared to the reference sequence (without addition or deletion) for the optimal alignment of the two sequences. The RuBisCo transit peptide is used to transfer a recombinant protein expressed in a transgenic plant into a chloroplast, and when the RuBisCo transit peptide is expressed, a part of the sequence is cut off, and only a part of the amino acids may remain. More specifically, when the recombinant PCV2 capsid protein fused with the RuBisCo transit peptide according to the present invention is expressed in a plant, 54 amino acids on the front side of the RuBisCo transit peptide are cut off, and only the amino acid sequence represented by SEQ ID NO: 1 may remain. Further, in this case, an additional amino acid may be inserted between a RuBisCo transit peptide sequence and a polyhistidine sequence to combine the DNA frames, and preferably, glycine or isoleucine may be further inserted.

As used herein, the term "chaperone binding protein (BiP)" is used to transfer the expressed recombinant protein into the endoplasmic reticulum, is preferably a gene including a base sequence of SEQ ID NO: 10, and most preferably a gene represented by SEQ ID NO: 10, but may include a base sequence having a sequence homology of 80% or more, more preferably 90% or more, and even more preferably 95% or more to the base sequence of SEQ ID NO: 10. When the BiP gene is expressed, a part of the sequence is cut off, and only a part of the amino acids may remain.

As used herein, the term "transit peptide" or "signal peptide" refers to an amino acid sequence that can induce the transport or localization of a protein to specific organelles, cell compartments, and extracellular transport sites. The term includes both transit peptides and all nucleotide sequences encoding the transit peptides.

As used herein, the term "PCV2" refers to porcine circovirus type 2, is a small (17 to 22 nm in diameter) icosahedral non-enveloped DNA virus, and contains a single-stranded circular genome. PCV2 shares approximately 80% sequence identity to Porcine Circovirus Type 1 (PCV1). However, generally in contrast to non-toxic PCV1, pigs infected with PCV2 typically exhibit the symptoms called post-weaning multisystemic wasting syndrome (PMWS). PCV2 has two major open reading frames (ORFs). ORF produces a viral replication protein (Rep), and ORF2 produces a "capsid protein". For the capsid protein produced by transcribing ORF2 of PCV2, three capsid proteins are gathered to form one face, and 20 faces are assembled to form an icosahedral structure, thereby completing a structure of virus-like particles (VLPs). PCV2 may be divided into genotypes such as PCV2a, PCV2b, and PCV2c according to the genotype of ORF2 encoding the capsid protein. However, the pathogenicity among such genotypes is not yet clear, and the results through artificial infection have not led to a conclusion on the difference in pathogenicity.

PCV2a and PCV2b are collectively referred to as "PCV2" in the present specification, but preferably mean PCV2a. Further, if necessary, PCV2 was divided into and referred to as PCV2a and PCV2b, respectively, when comparison between genotypes was required.

As used herein, the term "polynucleotide" refers to an oligomer or polymer containing two or more linked nucleotides or nucleotide derivatives generally bound to each other via a phosphodiester bond, including deoxyribonucleic acid (DNA) and ribonucleic acid (RNA). The polynucleotide also includes DNA and RNA derivatives including, for example, a nucleotide analog or a backbone bond other than a phosphodiester bond, for example, a phosphotriester bond, a phosphoramidate bond, a phosphorothioate bond, a thioester bond, or a peptide bond (peptide nucleic acid). The polynucleotide includes single-stranded and/or double-stranded polynucleotides, for example, deoxyribonucleic acid (DNA) and ribonucleic acid (RNA) as well as analogs of either RNA or DNA.

As used herein, the term "vector" refers to a DNA preparation containing a DNA sequence operably linked to a suitable regulatory sequence capable of expressing the DNA in a suitable host. The vector may be a plasmid, a phage particle, or simply a potential genomic insert. Once transformed into a suitable host, the vector may be replicated and function independently of the host genome, or may be integrated into the genome itself in some cases. Since the plasmid is currently the most commonly used type of vector, the terms plasmid and vector may be sometimes used interchangeably. However, the present invention includes other forms of known vectors having functions equivalent to those known in the art or have become known.

A polynucleotide encoding the RuBisCo peptide of the present invention may include a base sequence represented by SEQ ID NO: 2, and further, a polynucleotide encoding a PCV2 capsid protein may include a base sequence represented by SEQ ID NO: 4 or 6. In addition, the polynucleotide encoding the RuBisCo peptide of the present invention includes a variant of SEQ ID NO: 2 within the scope of the present invention. Specifically, the polynucleotide may include a base sequence having a sequence homology of 90% or more, more preferably 95% or more, and most preferably 98% or more to a base sequence of SEQ ID NO: 2. Furthermore, a polynucleotide encoding the PCV2 protein of the present invention includes a variant of SEQ ID NO: 4 or 6 within the scope of the present invention. Specifically, the polynucleotide may include a base sequence having a sequence homology of 90% or more, more preferably 95% or more, and most preferably 98% or more to a base sequence of SEQ ID NO: 4 or 6.

Further, the recombinant vector of the present invention may further include a polynucleotide encoding a polyhistidine-tag including an amino acid sequence represented by SEQ ID NO: 7.

In addition to PCV2, which is the target protein of the present invention, the polyhistidine-tag is further included for easy isolation, and representatively, an Avi tag, Calmodulin tag, polyglutamate tag, E tag. FLAG tag, HA tag, Myc tag. S tag, SBP tag, IgG Fc tag, CTB tag, Softag 1 tag, Softag 3 tag, Strep tag, TC tag, V5 tag, VSV tag, Xpress tag, and the like may be included.

In addition, in the recombinant vector, a polynucleotide encoding RuBisCO transit peptide, a polynucleotide encoding a polyhistidine-tag, and a polynucleotide encoding a PCV2 capsid protein are sequentially connected between a promoter and a terminator, but the order of connection is not limited thereto.

Examples of the promoter include a pEMU promoter, a MAS promoter, a histone promoter, a Clp promoter, a cauliflower mosaic virus-derived 35S promoter, a cauliflower mosaic virus-derived 19S RNA promoter, an actin protein promoter of a plant, a ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, and the like, examples of the terminator include a nopaline synthase (NOS) terminator, a rice amylase RAmy1A terminator, a phaseoline terminator, a terminator of an octopine gene of *Agrobacterium tumefaciens*, a rrnB1/B2 terminator of *E. coli*, and the like, but the examples are illustrative only and are not limited thereto.

As another aspect of the present invention, a transgenic plant transformed with the recombinant vector according to the present invention may be provided.

As used herein, the "transformation" collectively refers to those processes in which genetic properties of a living organism are changed by injected DNA, the "transgenic plant" is a plant prepared by injecting an external gene by a molecular genetic method and is preferably a plant transformed by a recombinant expression vector of the present invention, and the plant is not limited as long as the plant achieves the object of the present invention.

Furthermore, the transgenic plant according to the present invention may be prepared by a method such as transformation, transfection, *Agrobacterium*-mediated transformation, particle gun bombardment, sonication, electroporation, and polyethylene glycol (PEG)-mediated transformation, but there is no limitation as long as it is a method capable of injecting the vector of the present invention.

As another aspect of the present invention, the present invention provides a method for isolating and purifying a recombinant PCV2 capsid protein, the method including the following steps:

(S1) transforming a plant using the recombinant vector of the present invention;

(S2) preparing a plant mixture solution by mixing the transgenic plant obtained in Step (S1) with a protein extraction buffer solution:

(S3) adsorbing a recombinant protein in which a polyhistidine-tag is linked to the PCV2 capsid protein by injecting the mixture solution obtained in Step (S2) into a column packed with agarose;

(S4) washing the column by injecting a washing solution into the column; and (S5) eluting the recombinant protein adsorbed onto agarose by injecting an elution solution into the column.

The protein extraction buffer solution according to the present invention may include 10 to 100 mM Tris, 100 to 300 mM sodium chloride (NaCl), 0.01 to 0.5% Triton X-100(polyethylene glycol p-(1,1,3,3-tetramethylbutyl)-phenylether, and 5 to 300 mM imidazole.

The agarose according to the present invention may be nickel-nitrilotriacetic acid (Ni-NTA) agarose.

Further, in the present invention, Step (S1) may transform a plant using a bacterium into which a recombinant vector is introduced, and the bacterium may be preferably *Agrobacterium tumefaciens*.

As still another aspect of the present invention, provided is a method for preparing a vaccine composition containing virus-like particles, the method including the following steps:

(S1) transforming a plant using the recombinant vector of the present invention;

(S2) isolating and purifying a PCV2 capsid protein from the transgenic plant obtained in Step (S1);

(S3) making the PCV2 capsid protein obtained in Step (S2) into virus-like particles; and (S4) preparing a vaccine composition containing the virus-like particles obtained in Step (S3).

As used herein, the term "vaccine" is a biological preparation containing an antigen that causes an immune response in an organism, and refers to an immunogen that induces immunity in an organism by injection or oral administration into a human or animal for prevention of an infectious disease. The animal is a human or non-human animal, and the non-human animal refers to a pig, a cow, a horse, a dog, a goat, sheep, and the like, but is not limited thereto.

The "vaccine composition" of the present invention may be used by being formulated in the form of an oral formulation such as a powder, a granule, a tablet, a capsule, a suspension, an emulsion, a syrup, and an aerosol, and a sterile injection solution, according to a typical method. When the composition is prepared, the composition may be prepared using a commonly used diluent or excipient, such as a filler, an extender, a binder, a wetting agent, a disintegrant, and a surfactant. A solid formulation for oral formulation includes a tablet, a pill, a powder, a granule, and the like, and the solid formulation may be prepared by mixing at least one excipient, for example, starch, calcium carbonate, sucrose or lactose, gelatin, and the like with a lecithin-like emulsifier. Further, in addition to simple excipients, lubricants such as magnesium stearate and talc may also be used. As a liquid formulation for oral administration, a suspension, a liquid for internal use, an emulsion, a syrup, and the like may be used, and in addition to water and liquid paraffin which are simple commonly used diluents, various excipients, for example, a wetting agent, a sweetener, an aromatic, a preservative, and the like may be included. Examples of a formulation for parenteral administration include an aqueous sterile solution, a non-aqueous solvent, a suspension, an emulsion, and a freeze-dried preparation. As the non-aqueous solvent and the suspension, it is possible to use propylene glycol, polyethylene glycol, a vegetable oil such as olive oil, an injectable ester such as ethyl oleate, and the like.

The route of administration of the vaccine composition according to the present invention includes, but is not limited to, oral, intravenous, intramuscular, intraarterial, intramedullary, intrathecal, intracardiac, transdermal, subcutaneous, intraperitoneal, intranasal, intestinal canal, topical, sublingual or rectal routes. Oral or parenteral administration is preferred. As used herein, the term "parenteral" includes subcutaneous, intradermal, intravenous, intramuscular, intraarticular, intrasynovial, intrasternal, intrathecal, intralesional and intracranial injection or infusion techniques. The vaccine composition of the present invention may also be administered in the form of a suppository for rectal administration.

The dose of the vaccine composition or pharmaceutical composition according to the present invention is selected in consideration of the age, body weight, sex, physical condition and the like of an individual. The amount required to induce an immunoprotective response in an individual without particular side effects may vary depending on the recombinant protein used as an immunogen and the presence of a random excipient.

In the present invention, the method for preparing a vaccine composition may further include adding an adjuvant.

As used herein, the term "adjuvant" refers to a material or composition which may be added to a vaccine or pharmaceutically active components to increase or affect the immune response. Representatively, the adjuvant typically refers to a carrier or auxiliary material for an immunogen and/or another pharmaceutically active material or composition. Typically, the term "adjuvant" should be interpreted as a broad concept, and refers to a wide range of materials or stratagems, which may enhance the immunogenicity of an antigen which is integrated into the adjuvant or administered with the adjuvant. Further, the adjuvant is not limited thereto, and may be divided into an immune potentiator, an antigen delivery system, or a combination thereof.

In addition, in the present invention, the plant may be a dicotyledonous plant selected from the group consisting of *Arabidopsis thaliana*, soybean, tobacco, eggplant, capsicum, potato, tomato, Chinese cabbage, cabbage, and lettuce; or a monocotyledonous plant selected from the group consisting of rice, barley, wheat, rye, corn, sugar cane, oats, and onion.

As used herein, the term "plant" can be used without limitation as long as it is a plant capable of mass-producing the recombinant protein of the present invention, but more specifically, may be selected from the plant group mentioned above, and may be preferably tobacco. The tobacco in the present invention is not particularly limited in type as long as it is a plant of the *Nicotiana* genus and can overexpress a protein, and the present invention can be carried out by selecting an appropriate variety according to the transformation method and the purpose of mass production of the protein. For example, a variety such as *Nicotiana benthamiana* L. or *Nicotiana tabacum* cv. *Xanthi* may be used.

In addition, in the present invention, Step (S1) may transform a plant using a bacterium into which a recombinant vector is introduced, and the bacterium may be preferably *Agrobacterium tumefaciens*, but is not limited thereto as described above.

Furthermore, in the present invention, Step (S3) may make virus-like particles by changing a pH of a buffer solution including a PCV2 capsid protein.

In the making of the virus-like particles, a process of exchanging and concentrating a buffer solution using a filter such that the recombinant PCV2 capsid protein can form virus-like particles by self-assembly may be performed.

The buffer solution may include 50 to 100 mM Tris, 300 to 1000 mM sodium chloride (NaCl), and 10 to 100 mM arginine, and may have a pH of be 6.9 to 7.5, preferably 7.2. Further, size-exclusion chromatography may be performed to purify self-assembled recombinant PCV2 virus-like particles.

As still another aspect of the present invention, the present invention provides a vaccine composition prepared by the preparation method according to the present invention.

The vaccine composition may further include an adjuvant. In addition, the adjuvant may be alum, but any type of aluminum salt suitable for use as an adjuvant may be used in the present invention. The aluminum salt includes aluminum hydroxide ($Al(OH)_3$), aluminum phosphate ($AlPO_4$), aluminum hydrochloride, aluminum sulfate, ammonium alum, potassium alum, aluminum silicate, and the like. Preferably, aluminum hydroxide or aluminum phosphate may be used as the aluminum salt adjuvant.

Furthermore, as yet another aspect of the present invention, the present invention provides PCV2 virus-like particles contained in the vaccine composition. The PCV2 virus-like particles are shown to have a molecular weight of about 2,000 kDa by size-exclusion chromatography and 669 kDa or more by polyacrylamide gel electrophoresis (Native-PAGE), and may be a spherical or ring form having a diameter of 10 nm or more and 40 nm or less, preferably 20 nm or more and 30 nm or less when stained by a negative staining method, and then observed by a transmission electron microscope. Here, the term "about" means±10%. Therefore, a molecular weight of about 2,000 kDa means 1,800 kDa to 2,200 kDa.

As yet another aspect of the present invention, the present invention provides a method for preventing porcine circovirus infection by administering a vaccine composition prepared by the preparation method according to the present invention to an individual.

As yet another aspect of the present invention, the present invention provides a use of a vaccine composition prepared by the preparation method according to the present invention for preventing porcine circovirus infection.

Further, as yet another aspect of the present invention, the present invention provides a use of a composition prepared by the preparation method according to the present invention for producing a vaccine used for preventing porcine circovirus infection.

Terms or words used in the specification and the claims should not be interpreted as being limited to a typical or dictionary meaning and should be interpreted with a meaning and a concept which conform to the technical spirit of the present invention based on the principle that an inventor can appropriately define a concept of a term in order to describe his/her own invention in the best way.

Hereinafter, preferred Examples for helping the understanding of the present invention will be suggested. Hereinafter, the following Examples are suggested to aid in understanding the present invention, and the contents of the present invention are not limited by the following Examples.

In the following Examples and drawings, PCV2 refers to PCV2a unless specifically mentioned as PCV2b.

EXAMPLES

Example 1: Construction of Plant Expression Vector for Expressing Recombinant PCV2 Capsid Protein As illustrated in the cleavage map of FIG. 1, a recombinant vector for plant expression was constructed so as to express a recombinant PCV2 capsid protein in a plant.

More specifically, genetic information on the PCV2 capsid protein was obtained, and a gene (SEQ ID NO: 4 or 6) was synthesized with a sequence optimized for expression in *Nicotiana benthamiana*. A chloroplast-targeted recombinant PCV2 capsid protein plant expression vector was constructed by sequentially linking a polynucleotide (SEQ ID NO: 2) encoding a RuBisCO transit peptide, a polynucleotide (SEQ ID NO: 8) encoding 6 consecutive histidines, and a polynucleotide (SEQ ID NO: 4 or 6) encoding a PCV2 capsid protein between a CaMV35S promoter of a pCAMBIA1300 vector and a NOS terminator. A chloroplast-targeted recombinant PCV2 capsid protein plant expression vector was constructed by sequentially linking a polynucleotide (SEQ ID NO: 10) encoding a chaperone binding protein (BiP) signal peptide, a polynucleotide (SEQ ID NO: 4 or 6) encoding a PCV2 capsid protein, a polynucleotide (SEQ ID NO: 8) encoding 6 consecutive histidines, and a polynucleotide (SEQ ID NO: 12) encoding a His-Asp-Glu-Leu (HDEL) peptide between a CaMV35S promoter of the pCAMBIA1300 vector and a NOS terminator.

Example 2: Confirmation of Expression of Recombinant PCV2 Capsid Protein 2.1. Transient Expression of Plant Expression Vector An *Agrobacterium* LBA4404 strain was transformed with the plant expression vectors prepared in Example 1 using an electric shock method (electroporation). After the transformed agrobacteria were shake-cultured in 5 mL of a YEP liquid medium (10 g of yeast extract, 10 g of peptone, 5 g of NaCl, 50 mg/L canamycin, and 25 mg/L rifampicin) under the condition of 28° C. for 16 hours, 1 ml of a primary culture medium was inoculated into 50 ml of a fresh YEP medium and shake-cultured under the condition of 28° C. for 6 hours. The agrobacteria thus cultured were collected by centrifugation (7,000 rpm, 4° C., 5 minutes), and then suspended in an infiltration buffer [10 mM MES (pH 5.7), 10 mM $MgCl_2$, and 200 µM acetosyringone]. Agro-infiltration was performed by a method of injecting the agrobacterial suspension into the backside of leaves of *Nicotiana benthamiana* using a syringe from which the injection needle had been removed.

2.2. Confirmation of Expression of Recombinant PCV2 Capsid Protein in Plant

After proteins were extracted from the plant leaves prepared in Example 2.1 and centrifuged, the expression of a recombinant PCV2 capsid protein was confirmed by western blotting by isolating a protein in a water-soluble fraction (Supernatant; S), a protein in a pellet (Pellet; P) fraction, and a fraction (Total; T) including both the water-soluble fraction and the pellet, respectively. More specifically, 30 µL of each fraction was mixed with an SDS sample buffer, and then heated. Next, protein bands separated by size were confirmed by subjecting a 10% SDS-PAGE gel to electrophoresis, the separated proteins were transferred to a PVDF membrane, and then subjected to a blocking step using 5% skim milk, and then the proteins were bound to an antibody reacting with polyhistidine, and treated with an ECL solution by the method provided by the manufacturer, thereby confirming the expression of a recombinant PCV2 capsid protein.

Figure 2:
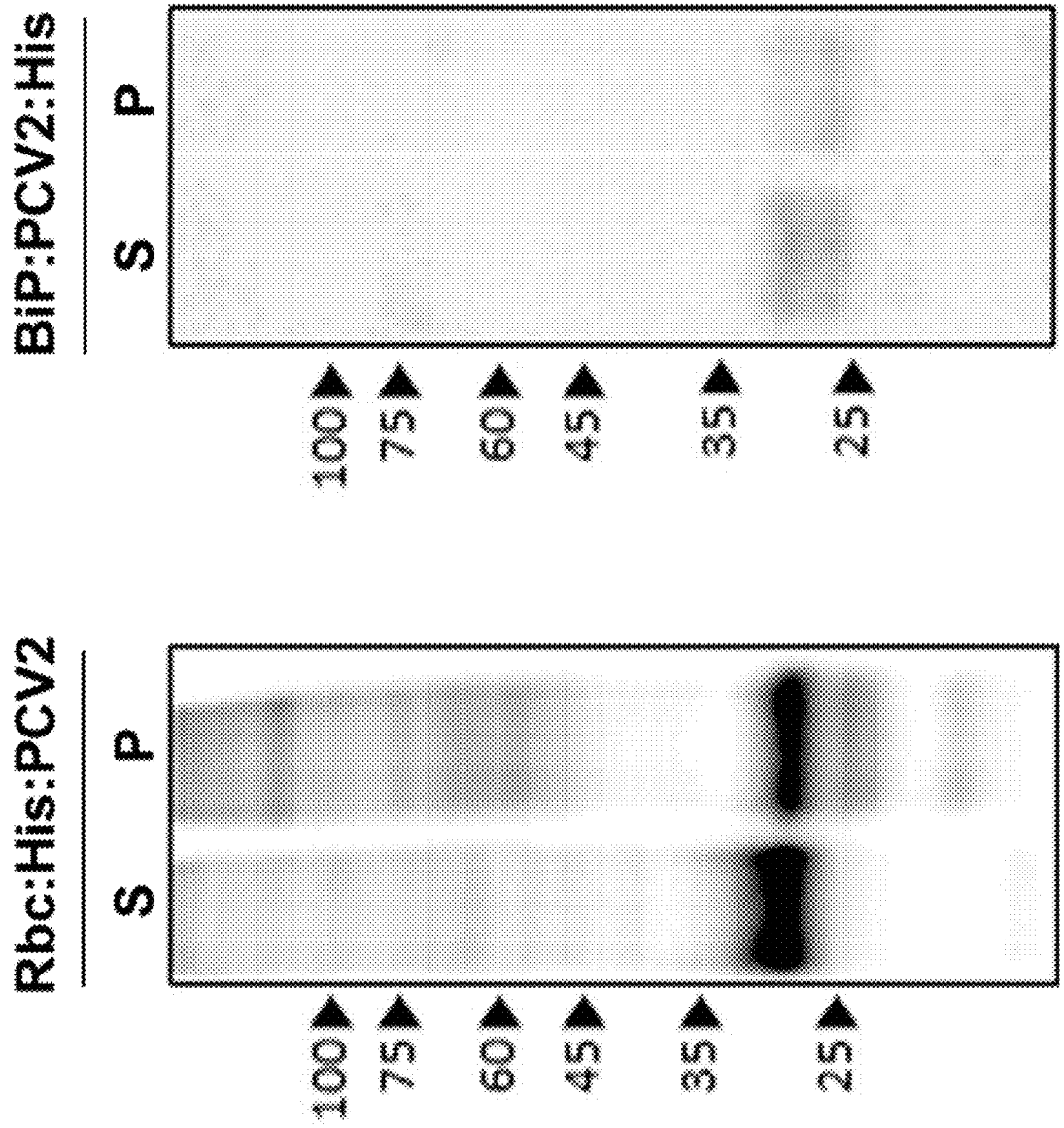
FIG. 2 is a view illustrating the results of confirming the expression of two recombinant PCV2 capsid proteins in a plant according to an exemplary embodiment of the present invention by western blotting.
Figure 3:
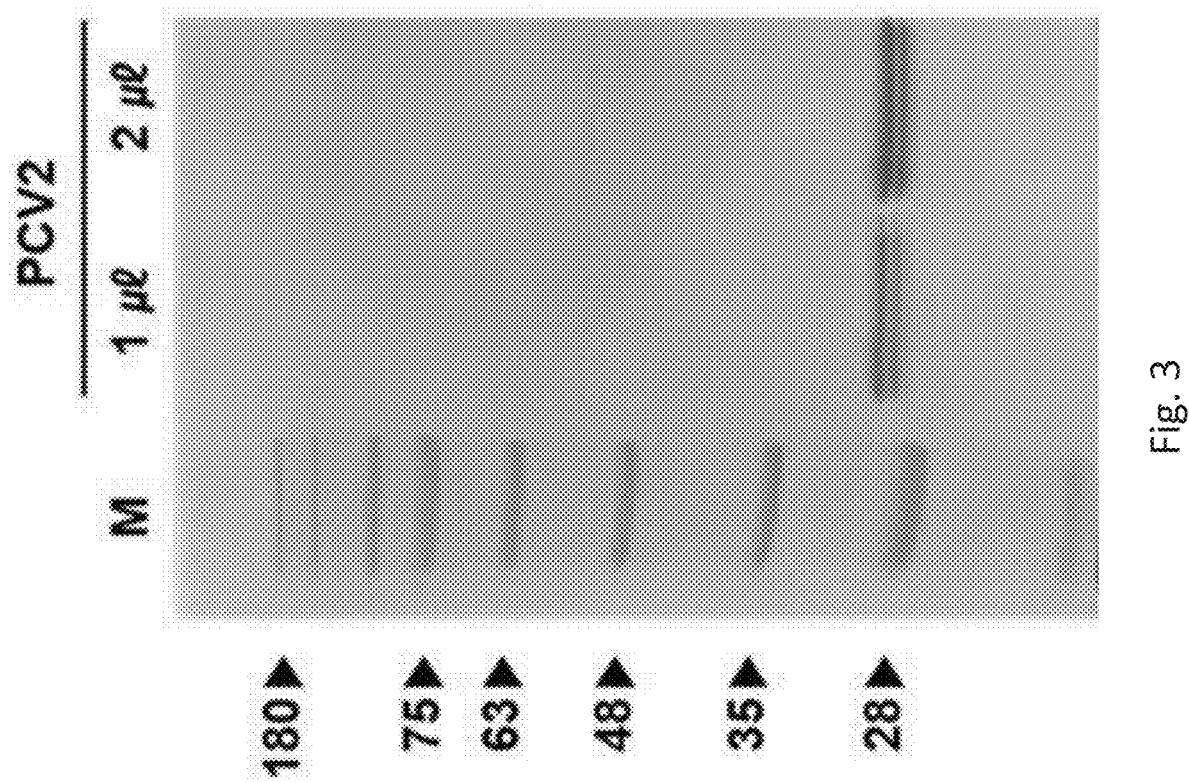
FIG. 3 is a view illustrating the results of isolation and purification of the recombinant PCV2 capsid protein according to an exemplary embodiment of the present invention using affinity chromatography.
Figure 4:
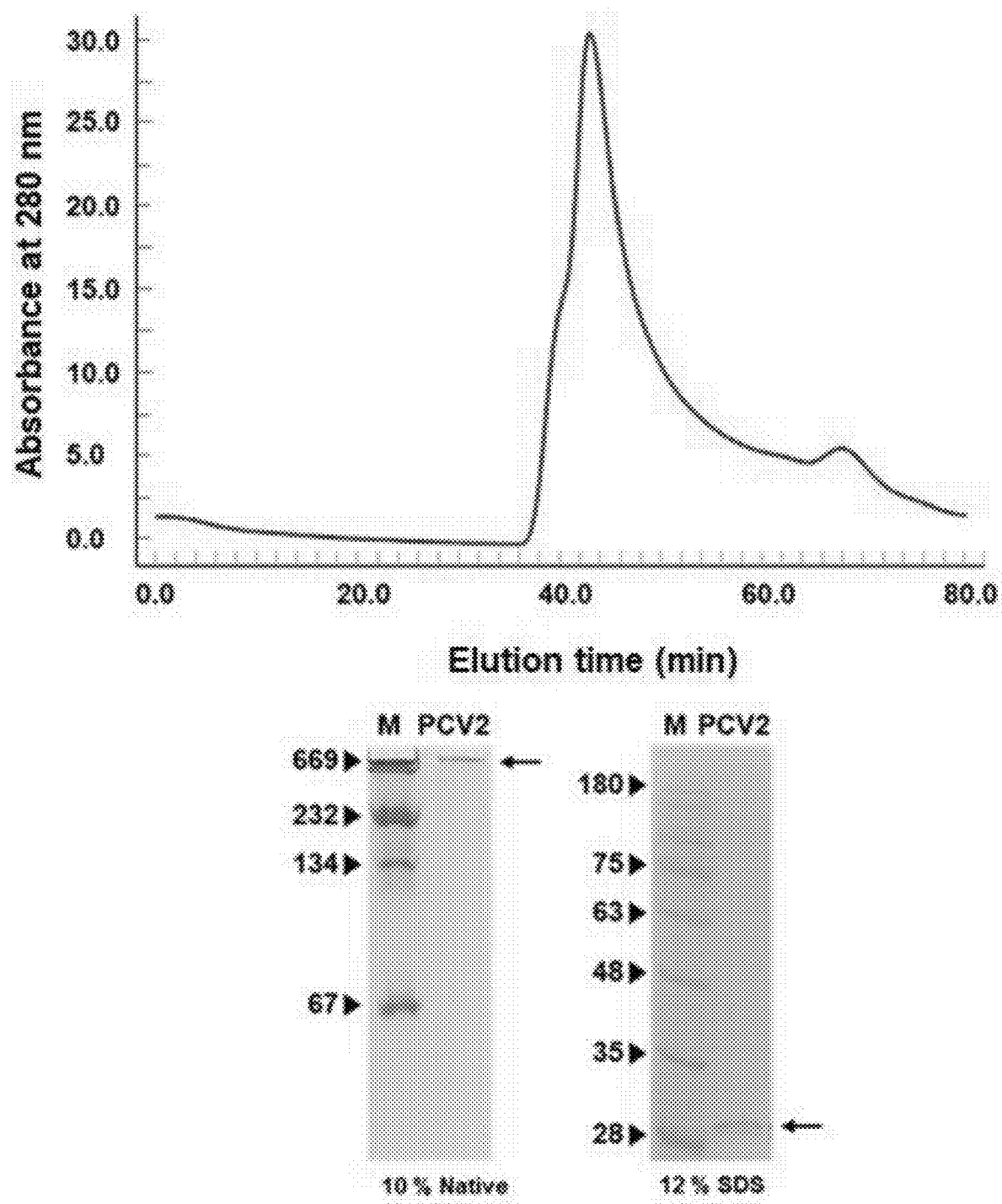
FIG. 4 is a view illustrating the results of size-exclusion chromatography and Native-PAGE and SDS-PAGE of the recombinant PCV2 capsid protein isolated and purified in the present invention.
Figure 5:
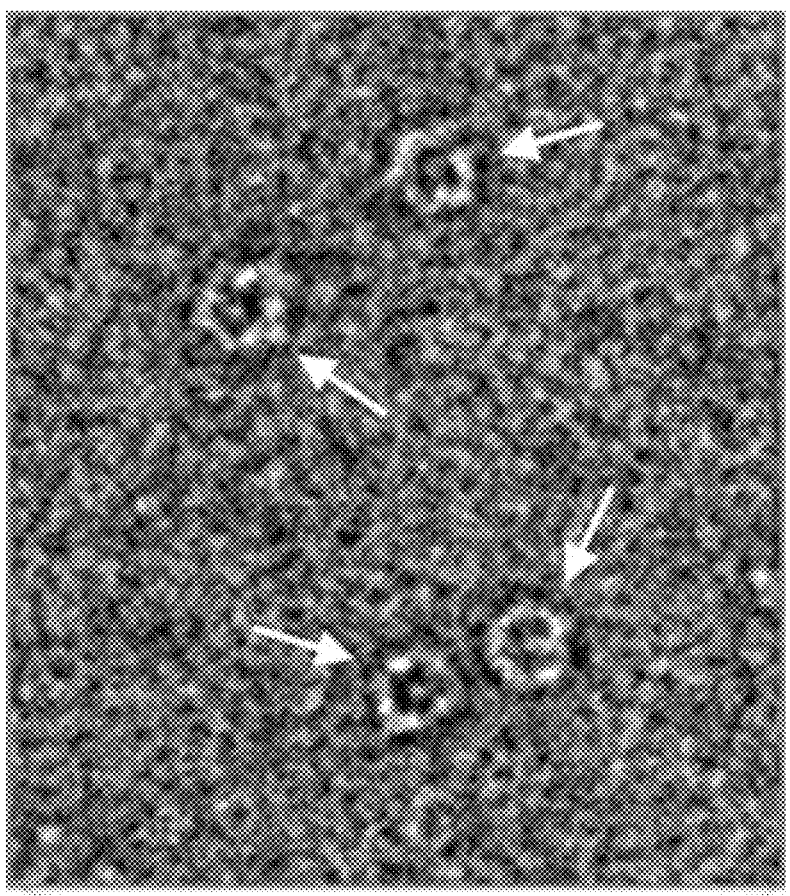
FIG. 5 is a view illustrating images of virus-like particles formed by the recombinant PCV2 capsid protein isolated and purified in the present invention taken by a transmission electron microscope.
Figure 5:
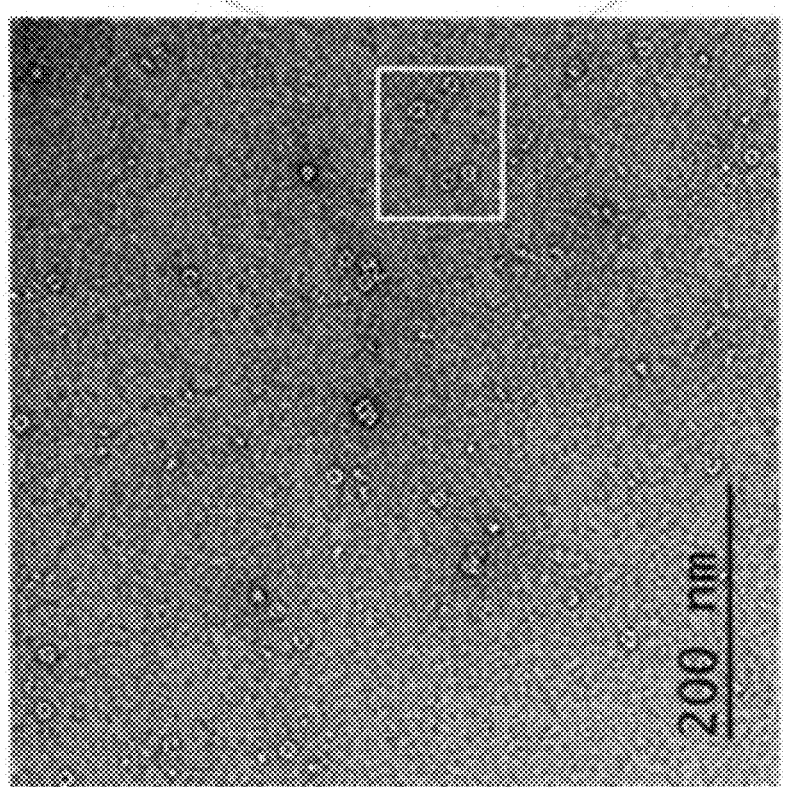
Figure 6:
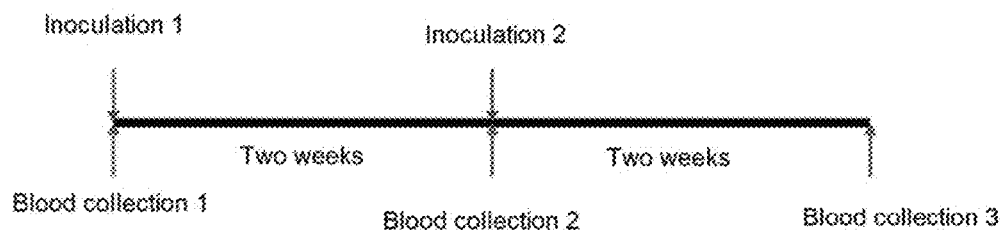
FIG. 6 is a view (top) illustrating a guinea pig experimental method for confirming whether an antibody of the recombinant PCV2 capsid protein isolated and purified in the present invention with a chart and a schematic view, and a view (bottom) illustrating the results confirmed by an ELISA kit with a bar graph.
Figure 6:
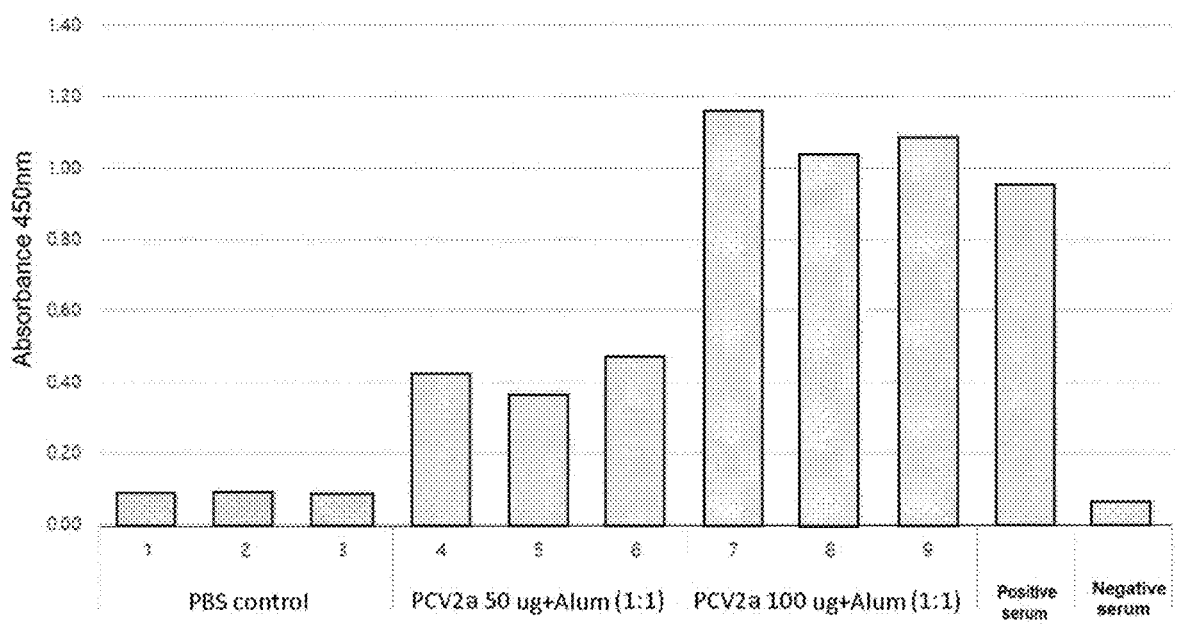

As a result, as illustrated in FIG. 2, it was confirmed that the recombinant PCV2 capsid protein fused with a RuBisCO transit peptide so as to be targeted to the chloroplast was expressed with high efficiency, 70% or more of the expressed recombinant PCV2 capsid protein was confirmed in the water-soluble fraction, and about 30% of the PCV2 capsid protein was observed in the pellet fraction (photo on the left side of FIG. 2). In comparison, the recombinant PCV2 capsid protein fused with the BiP signal peptide so as to be targeted to the endoplasmic reticulum had extremely low expression efficiency (photo on the right side of FIG. 2). Accordingly, the following examples were performed using only the recombinant PCV2 capsid protein fused with the chloroplast-targeted RuBisCO transit peptide.

Example 3: Isolation and Purification of Recombinant PCV2 Capsid Protein Expressed in Plant 100 mL g of a protein extract solution [50 mM Tris-HCl (pH 8.2), 300 mM NaCl, 10 mM imidazole, and 0.5% Triton X-100] was added to 50 g of *Nicotiana benthamiana* leaves expressing the recombinant PCV2 capsid protein prepared in Example 2.1, tissues were crushed by a blender, and then the protein extract solution was recovered by centrifugation at 13,000 rpm at 4° C. for 30 minutes. Affinity chromatography was performed with a column packed with a nickel-nitrilotriacetic acid (Ni-NTA) agarose resin for the isolation and purification of the recombinant PCV2 capsid protein from the protein extract solution. The column was packed with 10 mL of a resin, and then equilibrated with 100 mL of a washing solution [50 mM Tris-HCl (pH 8.2), 300 M NaCl, and 10 mM imidazole]. The recovered protein extract solution was applied to the column and equilibrated, and then the resin was washed by flowing 100 mL of the washing solution, and the recombinant PCV2 protein was eluted with an elution solution [50 mm Tris-HCl (pH 8.2), 300 mm NaCl, and 250 mM imidazole]. For the elution solution including the recombinant PCV2 capsid protein, buffer exchange and concentration were performed with a buffer solution for making virus-like particles [50 mm Tris-HCl (pH 7.4), 300 mM NaCl, 100 mM arginine, and a final pH was adjusted to 7.2] using a 30 kDa size filter. The isolated and purified recombinant PCV2 capsid protein was subjected to electrophoresis (SDS-PAGE), and then confirmed by Coomassie staining (see FIG. 3).

Example 4: Purification of Recombinant PCV2 Capsid Protein

The recombinant PCV2 capsid protein forms recombinant PCV2 virus-like particles through self-assembly. Therefore, size-exclusion chromatography was performed to isolate recombinant PCV2 virus-like particles. The size-exclusion chromatography (HiLoad 16/600 Superdex™ 200 pg) was equilibrated using an elution solution [50 mm Tris-Cl (pH 7.4), 300 mm NaCl, and 0.5 mM EDTA]. 5 mg of a buffer solution containing the isolated and purified recombinant PCV2 capsid protein obtained in Example 3 was loaded on a size-exclusion chromatography column, and separated by size to obtain a first peak fraction. Native-PAGE electrophoresis was performed on the obtained fractions to confirm whether virus-like particles were formed. In addition, SDS-PAGE electrophoresis was performed to confirm the degree of purification of the isolated and purified recombinant PCV2 capsid protein. The results of separation by the size-exclusion chromatography and the results of Native-PAGE and SDS-PAGE electrophoresis are illustrated in FIG. 4.

Example 5: Confirmation of Recombinant PCV2 Virus-Like Particle

Negative-staining was performed by diluting the recombinant PCV2a capsid protein included in the first and second fractions isolated by size-exclusion chromatography with an elution solution [50 mM Tris-Cl (pH 7.4), 300 mM NaCl, and 0.5 mM EDTA] such that the final concentration became 100 nM. After 5 μL of a protein solution was reacted on a carbon-coated copper grid for 1 minute, the protein solution was removed using a filter paper and washed 3 times with tertiary distilled water. In this case, the carbon-coated copper grid reacts with plasma for 1 minute to convert the hydrophobic properties into hydrophilic properties, making it easier for proteins to be attached to carbon. Finally, the grid was reacted with 1% uranyl acetate for 1 minute for negative staining, and then the staining solution was removed with a filter paper and dried at room temperature for 12 hours. Images at a magnification of 20,000 times were obtained from the prepared grid using a transmission electron microscope (Tecnai T10, Philips. Japan).

As a result, as illustrated in FIG. 5, virus-like particles consisting of the recombinant PCV2 capsid protein could be observed in the first fraction.

Example 6: Confirmation of Formation of Recombinant PCV2 Capsid Protein Antibody An experiment was conducted to confirm whether the composition containing the recombinant PCV2 virus-like particles confirmed in Example 5 formed an antibody, and conducted in accordance with the Korean standard assay of veterinary biological products [1-2-04-03 Porcine Circovirus Type2 gene recombinant inactivated vaccine (PCV2 antibody titer test)]. Nine guinea pigs weighing 300 to 350 g were prepared, a ½ dose was inoculated intramuscularly into three animals as a control and six animals as an experimental group, and a second inoculation was performed 2 weeks later. Here, the control refers to a group in which 1 ml of PBS alone was administered without an antigen, and the experimental group refers to a group in which 50% aluminum hydroxide gel was added to 50 μg and 100 μg of the PCV2 antigen, respectively. Two weeks after the second inoculation, blood was collected along with the control of three animals and the antibody titer was measured by an ELISA kit. ELISA absorbance measurement was performed according to the manufacturer's test method. The antibody formation results are illustrated in FIG. 6.

As a result, as illustrated in FIG. 6, it could be confirmed that an antibody was formed in the body of the guinea pig as the composition containing the PCV2 virus-like particles was administered. Furthermore, as the dose of the composition was increased, the amount of antibody formed also tended to increase.

Example 7: Confirmation of Formation of Recombinant PCV2a Capsid Protein Neutralizing Antibody It was confirmed whether a PCV2 neutralizing antibody was formed using a vaccine composition in which an aluminum hydroxide ($Al(OH)_3$) adjuvant was added to the composition containing the PCV2 virus-like particles confirmed in Example 5. The experiment was performed in accordance with the Korean standard assay of veterinary biological products (1-2-04-03 Porcine Circovirus Type2 gene recombinant inactivated vaccine). Six guinea pigs weighing 300 to 350 g were prepared, a ½ dose was inoculated intramuscularly into two animals as a control and four animals as an experimental group, and a second inoculation was performed 2 weeks later. Two weeks after the second inoculation, blood was collected along with the control of two animals and it was confirmed by an indirect fluorescent antibody test (immuno-fluorescence assay) whether the antibody was formed. The results of the virus neutralizing experiment are shown in the following Table 1.

TABLE 1

| Individual No. | Group No. | Adjuvant | Neutralizing antibody titer by genotype of PCV2 | |
|---|---|---|---|---|
| | | | PCV2a | PCV2b |
| 1 | PBS | PBS | 0 | 4 |
| 2 | | | 0 | 4 |
| 3 | 1 | 50 μg | >256 | 64 |
| 4 | | Alum | >256 | 64 |
| 5 | 2 | 100 μg | >256 | >256 |
| 6 | | Alum | >256 | 128 |

As a result, as shown in Table 1, it was confirmed that both PCV2 genotypes PCV2a and PCV2b have virus neutralizing ability. Furthermore, the virus neutralizing ability of PCV2a was generally better than that of PCV2b, and when 100 μg of an alum adjuvant was added, the neutralizing antibody titer was shown to be the highest.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described examples are illustrative only in all aspects and are not restrictive.

INDUSTRIAL APPLICABILITY

When the plant expression vector according to the present invention is used, it is advantageous in that the production costs can be remarkably reduced, contaminants such as viruses, oncogenes, and enterotoxins can be fundamentally blocked, and a synthetic route for an eukaryotic protein in which a post-translational transformation process occurs, and thus it is possible to produce a protein that maintains physiological activity, and even in the commercialization stage, the product can be managed as a seed stock. Furthermore, when the demand for the corresponding material increases rapidly, the present invention is more efficient and economical than an existing production system using animal cells or bacteria in terms of equipment technology and costs required for mass production, so that it is expected to have great industrial applicability value in that the corresponding material can be mass-produced and supplied in a short period of time as demand arises.

The invention claimed is:

1. A recombinant vector for plant expression, comprising a polynucleotide encoding a RuBisCO transit peptide comprising the amino acid sequence of SEQ ID NO: 1 and a polynucleotide consisting of the nucleotide sequence of SEQ ID NO: 4 encoding a porcine circovirus type 2 (PCV2) capsid protein.

2. The recombinant vector of claim 1, wherein the polynucleotide encoding the RuBisCO transit peptide comprises the nucleotide sequence of SEQ ID NO: 2.

3. The recombinant vector of claim 1, further comprising a polynucleotide encoding a polyhistidine-tag comprising the amino acid sequence of SEQ ID NO: 7.

4. The recombinant vector of claim 3, wherein in the recombinant vector, the polynucleotide encoding the RuBisCO transit peptide, the polynucleotide encoding the polyhistidine-tag, and the polynucleotide encoding the PCV2 capsid protein are sequentially connected between a promoter and a terminator.

5. A transgenic plant transformed with the recombinant vector of claim 1.

6. A method for preparing a vaccine composition containing virus-like particles, the method comprising the following steps: (S1) transforming a plant using the recombinant vector of claim 1; (S2) isolating and purifying a PCV2 capsid protein from the transgenic plant obtained in Step (S1); (S3) making the PCV2 capsid protein obtained in Step (S2) into virus-like particles; and (S4) preparing a vaccine composition containing the virus-like particles obtained in Step (S3), wherein the virus-like particles are shown to have a molecular weight of 1,800 kDa or more and 2,200 kDa or less by size-exclusion chromatography and 669 kDa or more by Native-polyacrylamide gel electrophoresis, and are a spherical or ring form having a diameter of 20 nm to 30 nm when stained by a negative staining method and observed by a transmission electron microscope.

7. The method of claim 6, further comprising adding an adjuvant.

8. The method of claim 6, wherein the plant is a dicotyledonous plant selected from the group consisting of *Arabidopsis thaliana*, soybean, tobacco, eggplant, capsicum, potato, tomato, Chinese cabbage, cabbage, and lettuce; or a monocotyledonous plant selected from the group consisting of rice, barley, wheat, rye, corn, sugar cane, oats, and onion.

9. The method of claim 6, wherein Step (S1) transforms a plant using a bacterium into which a recombinant vector is introduced.

10. The method of claim 9, wherein the bacterium is *Agrobacterium tumefaciens*.

11. The method of claim 6, wherein Step (S3) makes virus-like particles by changing a pH of a buffer solution including a PCV2 capsid protein.

12. The method of claim 11, wherein the buffer solution comprises 50 to 100 mM Tris, 300 to 1000 mM sodium chloride (NaCl), and 10 to 100 mM arginine, and has a pH of 6.9 to 7.5.

13. The method of claim 12, wherein the pH is 7.2.

14. The method of claim 6, wherein the vaccine composition induces neutralizing antibodies against PCV2.

15. The method of claim 14, wherein the vaccine composition further comprises an adjuvant.

16. The method of claim 15, wherein the adjuvant is alum.

17. The method of claim 6, wherein step (S2) isolates and purifies the PCV2 capsid protein using a method that comprises the following steps: (P1) preparing a plant mixture solution by mixing the transgenic plant obtained in Step (S1) with a protein extraction buffer solution; (P2) adsorbing a recombinant protein in which a polyhistidine-tag is linked to the PCV2 capsid protein by injecting the mixture solution obtained in Step (P1) into a column packed with agarose; (P3) washing the column by injecting a washing solution into the column; and (P4) eluting the recombinant protein adsorbed onto agarose by injecting an elution solution into the column.

18. The method of claim 17, wherein the protein extraction buffer solution comprises 10 to 100 mM Tris, 100 to 300 mM sodium chloride (NaCl), 0.01 to 0.5% Triton X-100 (polyethylene glycol p-(1,1,3,3-tetramethylbutyl)-phenylether, and 5 to 300 mM imidazole.

19. The method of claim 17, wherein the agarose is nickel-nitrilotriacetic acid (Ni-NTA) agarose.

* * * * *